United States Patent [19]

Kelly

[11] 4,233,225
[45] Nov. 11, 1980

[54] 2-DECARBOXY-2-HYDROXYMETHYL-9-DEOXY-6,9α-EPOXYMETHANO-5,6-DIDEHYDRO-PGF$_1$ COMPOUNDS

[75] Inventor: Robert C. Kelly, Kalamazoo, Mich.

[73] Assignee: The Upjohn Company, Kalamazoo, Mich.

[21] Appl. No.: 67,494

[22] Filed: Aug. 16, 1979

Related U.S. Application Data

[60] Division of Ser. No. 935,392, Aug. 21, 1978, which is a division of Ser. No. 819,941, Jul. 28, 1977, Pat. No. 4,124,599, which is a continuation-in-part of Ser. No. 725,547, Sep. 22, 1976, abandoned, which is a continuation-in-part of Ser. No. 716,771, Aug. 23, 1976, abandoned.

[51] Int. Cl.$^3$ ............................................. C07D 311/02
[52] U.S. Cl. .................................................. 260/345.2
[58] Field of Search ....................................... 260/345.2

[56] References Cited
PUBLICATIONS

Pace-Asciak et al., Biochem., 10, 3657 (1971).
Pace-Asciak et al. Jacs., 98, 2348 (1976).

Primary Examiner—Nicky Chan
Attorney, Agent, or Firm—Robert A. Armitage

[57] ABSTRACT

The present invention relates to novel 2-decarboxy-2-hydroxymethyl-9-deoxy-6,9α-epoxymethano-5,6-didehydro-PGF$_1$ compounds, which are useful for inducing a variety of prostacyclin-like pharmacological effects. Accordingly, these compounds are useful pharmacological agents for the same purposes for which prostacyclin is employed.

13 Claims, No Drawings

2-DECARBOXY-2-HYDROXYMETHYL-9-DEOXY-6,9α-EPOXYMETHANO-5,6-DIDEHYDRO-PGF₁ COMPOUNDS

CROSS REFERENCE TO RELATED APPLICATION

The present application is a divisional application of U.S. Ser. No. 935,392, filed Aug. 21, 1978, now pending issuance as a U.S. patent; which is a divisional application of U.S. Ser. No. 819,941, filed July 28, 1977, now U.S. Pat. No. 4,124,599; which is a continuation-in-part application of U.S. Ser. No. 725,547, filed Sept. 22, 1976, now abandoned; which is a continuation-in-part application of U.S. Ser. No. 716,771, filed Aug. 23, 1976, now abandoned.

BACKGROUND OF THE INVENTION

The present invention relates to novel 2-decarboxy-2-hydroxymethyl-9-deoxy-6,9α-epoxymethano-5,6-didehydro-PGF₁ compounds, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention is incorporated here by reference from U.S. Pat. No. 4,124,599.

SUMMARY OF THE INVENTION

The present invention particularly provides a 5E compound of the formula

[chemical structure]

wherein $W_1$ is α—OH:β—H, α—H:β—OH, oxo, methylene, α—H:β—H, α—CH₂OH:β—H;
wherein L is
  (1) —(CH₂)$_d$—C(R₂)₂,
  (2) —CH₂—O—CH₂—Y—, or
  (3) —CH₂CH=CH—,
wherein d is zero to 5, $R_2$ is hydrogen, methyl, or fluoro, being the same or different with the proviso that one $R_2$ is not methyl when the other is fluoro, and Y is a valence bond, —CH₂— or —(CH₂)₂—,
wherein Q is oxo, α—H:β—H, α—OH:β—R₈ or α—R₈:β—OH;
wherein $R_8$ is hydrogen or alkyl of one to 4 carbon atoms, inclusive; and
wherein X is
  (1) trans—CH=CH—,
  (2) cis—CH=CH—,
  (3) —C≡C—, or
  (4) —CH₂CH₂—;
including the lower alkanoates thereof; and a 5Z compound of the formula

[chemical structure]

wherein $W_1$ is α—OH:β—H, α—H:β—OH, oxo, methylene, α—H:β—H, α—CH₂OH:β—H;
wherein L is
  (1) —(CH₂)$_d$—C(R₂)₂,
  (2) —CH₂—O—CH₂—Y—, or
  (3) —CH₂CH=CH—,
wherein d is zero to 5, $R_2$ is hydrogen, methyl, or fluoro, being the same or different with the proviso that one $R_2$ is not methyl when the other is fluoro, and Y is a valence bond, —CH₂— or —(CH₂)₂—,
wherein Q is oxo, α—H:β—H, α—OH:β—R₈ or α—R₈:β—OH
wherein $R_8$ is hydrogen or alkyl of one to 4 carbon atoms, inclusive, and
wherein X is
  (1) trans—CH=CH—,
  (2) cis—CH=CH—,
  (3) —C≡C—, or
  (4) —CH₂CH₂—;
including the lower alkanoates thereof.

With regard to the divalent substituents described in the claims, e.g., Q and $W_1$, these divalent radicals are defined as α—R$_i$:β—R$_j$, where R$_i$ represents a substituent of the divalent moiety of the alpha configuration with respect to the cyclopentane and R$_j$ represents a substituent of the divalent moiety of the beta configuration with respect to the cyclopentane ring. Accordingly, when Q is defined as α—OH:β—R₈, the hydroxy of the Q moiety is in the alpha configuration, i.e., as in prostacyclin, and the R₈ substituent is in the beta configuration. Not all carbon atoms to which such divalent moieties are attached represent asymmetric centers. For example, when both valence bonds are to hydrogen (e.g., $W_1$ or Q is α—H:β—H), then no asymmetric center is present.

DESCRIPTION OF THE PREFERRED EMBODIMENTS

The present invention particularly relates to the following chemical compound:
2-Decarboxy-2-hydroxymethyl-(5Z)-9-deoxy-6,9α-epoxymethano-Δ⁵-17,18-cis-didehydro-PGF₁.

I claim:
1. A 5E compound of the formula

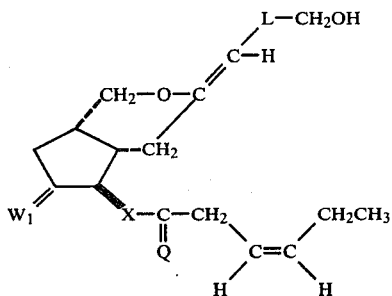

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;

wherein L is (1) —(CH$_2$)$_d$—C(R$_2$)$_2$, (2) —CH$_2$—O—CH$_2$—Y—, or (3) —CH$_2$CH=CH—, wherein d is zero to 5, $R_2$ is hydrogen, methyl, or fluoro, being the same or different with the proviso that one $R_2$ is not methyl when the other is fluoro, and Y is a valence bond, —CH$_2$— or —(CH$_2$)$_2$—, wherein Q is oxo, $\alpha$—H:$\beta$—H, $\alpha$—OH:$\beta$—R$_8$ or $\alpha$—R$_8$:$\beta$—OH wherein $R_8$ is hydrogen or alkyl of one to 4 carbon atoms, inclusive; and wherein X is (1) trans—CH=CH—, (2) cis—CH=CH—, (3) —C≡C—, or (4) —CH$_2$CH$_2$—;

including the lower alkanoates thereof.

2. A 5Z compound of the formula

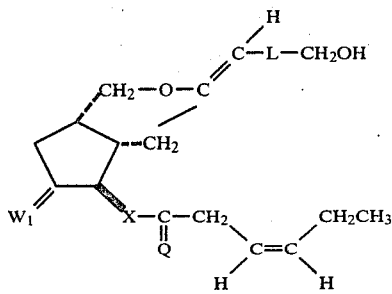

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;

wherein L is (1) —(CH$_2$)$_d$—C(R$_2$)$_2$, (2) —CH$_2$—O—CH$_2$—Y—, or (3) —CH$_2$CH=CH—, wherein d is zero to 5, $R_2$ is hydrogen, methyl, or fluoro, being the same or different with the proviso that one $R_2$ is not methyl when the other is fluoro, and Y is a valence bond, —CH$_2$— or —(CH$_2$)$_2$—, wherein Q is oxo, $\alpha$—H:$\beta$—H, $\alpha$—OH:$\beta$—R$_8$ or $\alpha$—R$_8$:$\beta$—OH wherein $R_8$ is hydrogen or alkyl of one to 4 carbon atoms, inclusive, and wherein X is (1) trans—CH=CH—, (2) cis—CH=CH—, (3) —C≡C—, or (4) —CH$_2$CH$_2$—;

including the lower alkanoates thereof.

3. 2-Decarboxy-2-hydroxymethyl-(5Z)-9-deoxy-6,9$\alpha$-epoxymethano-$\Delta^5$-17,18-cis-didehydro-PGF$_1$, a compound according to claim 2.

4. A compound according to claim 1 or 2, wherein $W_1$ is $\alpha$—H:$\beta$—OH.

5. A compound according to claim 1 or 2, wherein $W_1$ is oxo.

6. A compound according to claim 1 or 2, wherein $W_1$ is methylene.

7. A compound according to claim 1 or 2, wherein $W_1$ is $\alpha$—H:$\beta$—H.

8. A compound according to claim 1 or 2, wherein $W_1$ is $\alpha$—CH$_2$OH:$\beta$—H.

9. A compound according to claim 1 or 2, wherein $W_1$ is $\alpha$—OH:$\beta$—H.

10. A compound according to claim 9, wherein L is —(CH$_2$)$_n$—, n being 3, 4, or 5, wherein Q is oxo or $\alpha$—OH:$\beta$—R$_8$ and wherein $R_8$ is hydrogen, methyl, or ethyl.

11. A compound according to claim 10, wherein X is —C≡C—.

12. A compound according to claim 10, wherein X is —CH$_2$CH$_2$—.

13. A compound according to claim 10, wherein X is trans—CH=CH—.

* * * * *

UNITED STATES PATENT OFFICE
CERTIFICATE OF CORRECTION

Patent No. 4,233,225     Dated 11 November 1980

Inventor(s) Robert C. Kelly

It is certified that error appears in the above-identified patent and that said Letters Patent are hereby corrected as shown below:

Column 1, lines 33-34, "a 5E compound" should read -- a 5Z compound --;
Column 2, line 1, "a 5Z compound" should read -- a 5E compound --;
Column 2, line 68, "a 5E compound" should read -- a 5Z compound --;
Column 3, line 60, "a 5Z compound" should read -- a 5E compound --;
Column 4, line 37, "according to claim 2" should read -- according to claim 1 --.

Signed and Sealed this

Thirtieth Day of June 1981

[SEAL]

Attest:

RENE D. TEGTMEYER

Attesting Officer     Acting Commissioner of Patents and Trademarks